United States Patent
Hitomi et al.

Patent Number: 5,415,760
Date of Patent: May 16, 1995

[54] GALVANIC CELL TYPE GAS CONCENTRATION SENSOR SYSTEM CAPABLE OF DETECTING MORE THAN ONE TYPE OF GAS

[75] Inventors: Shuji Hitomi; Hisashi Kudo, both of Kyoto, Japan

[73] Assignee: Japan Storage Battery Company Limited, Kyoto, Japan

[21] Appl. No.: 43,755

[22] Filed: Apr. 7, 1993

[30] Foreign Application Priority Data

May 20, 1992 [JP] Japan .................. 4-154290
Jun. 2, 1992 [JP] Japan .................. 4-168555

[51] Int. Cl.⁶ .......................... G01N 27/404
[52] U.S. Cl. ...................... 204/415; 204/412; 204/431
[58] Field of Search ............. 204/400, 412, 415, 431

[56] References Cited

U.S. PATENT DOCUMENTS

| Re. 31,914 | 6/1985 | Oswin et al. | 204/153.2 |
|---|---|---|---|
| 3,503,861 | 3/1970 | Volpe | 204/415 |
| 3,556,950 | 1/1971 | Dahms | 204/409 |
| 3,622,487 | 11/1971 | Chand et al. | 204/153.14 |
| 3,902,982 | 9/1975 | Nakagawa | 204/286 |
| 4,568,445 | 2/1986 | Cates et al. | 204/415 |

FOREIGN PATENT DOCUMENTS

| 0027005 | 9/1980 | European Pat. Off. |
|---|---|---|
| 0122511 | 3/1984 | European Pat. Off. |
| 0293541 | 6/1987 | European Pat. Off. |
| 3186754 | 8/1991 | Japan. |
| 2001763 | 7/1978 | United Kingdom. |

Primary Examiner—T. Tung
Attorney, Agent, or Firm—Sughrue, Mion, Zinn, Macpeak & Seas

[57] ABSTRACT

A galvanic cell type gas sensor which utilizes the respective merits of galvanic cell type and polaro type gas sensors so that a plurality of gasses can be detected by one sensor. One working electrode is utilized in conjunction with two or more counter electrodes which are different in kind from each other. Each of the electrodes are individually selected corresponding to a type of gas to be detected. Also, drift in the measurement of one of the detected gasses can be corrected based upon the measurement of another of the detected gasses.

5 Claims, 5 Drawing Sheets

GALVANIC CELL TYPE GAS CONCENTRATION SENSOR SYSTEM CAPABLE OF DETECTING MORE THAN ONE TYPE OF GAS

BACKGROUND OF THE INVENTION

1. Field of the Invention

The present invention relates to a gas concentration meter system for measuring the concentration of a gas or a dissolved gas in liquid phase, and particularly relates to a galvanic cell type gas sensor system capable of detecting a plurality of different gasses.

2. Description of the Related Art

Galvanic cell type, or polaro type, gas sensors which operate at ordinary temperatures so as to be easy to handle are generally used for measuring the amount of a specific gas in air or water.

The galvanic cell type sensor is basically constituted by a working electrode composed of a catalyst electrode for provoking an electrochemical oxidation/reduction reaction on an objective gas, a diaphragm for limiting the supply of the gas, a counter electrode formed from reducing/oxidizing active materials, an electrolytic solution, and a container for containing the aforementioned members. Gas concentration is determined from the value of a current by taking advantage of the phenomenon that the current between a working electrode and a counter electrode is proportional to the gas concentration when electrical discharge occurs between the working electrode and the counter electrode through a resistor selected to provoke an electrochemical oxidation/reduction reaction in the diffusion-controlling rate region of the objective gas.

The gas equilibrium potential varies according to the type of gas. In the galvanic cell type gas sensor in which the potential of the working electrode greatly depends on the potential of the counter electrode, selection of the counter electrode is very important. This is so because if the counter electrode is not properly selected, it is impossible to obtain the aforementioned diffusion-controlling rate region. Also, in such a case, oxygen or hydrogen may be produced from the working electrode so as to allow current flow regardless of the concentration of the objective gas. Therefore, in the case where a plurality of gasses are to be detected, a plurality of sensors having various counter electrodes and various electrolytic solutions must be respectively prepared, each corresponding a type of gas to be detected.

A polaro type sensor is the same in basic structure as the galvanic cell type gas sensor described above, but different from the latter in that the operating potential of the working electrode is set by using an external variable voltage supply. Therefore, the potential of the working electrode can be selected freely so as to establish a diffusion-controlling rate region and avoid the production of oxygen or hydrogen. Accordingly, detection of a plurality of gasses can be performed by using one sensor.

The galvanic cell type gas sensor which theoretically utilizes a battery reaction provides an output by itself, so that it is unnecessary to use an external electric power source for driving the sensor. In order to detect a plurality of gasses as described above, however, a plurality of sensors having different counter electrodes are required. On the other hand, the polaro type gas sensor requires a constant potential application device such as a potentiostat which is expensive and difficult to handle as well as an electric source for driving the device. However, with a polaro type sensor a plurality of gasses can be detected by one sensor by changing the potential of the working electrode.

SUMMARY OF THE INVENTION

An object of the present invention is to provide a galvanic cell type gas sensor which achieves the respective advantages of both the galvanic cell type and polaro type gas sensors so that a plurality of gasses can be detected by one sensor without the need for an external voltage supply.

Another object of the invention is to provide a galvanic cell type gas sensor which can be easily and accurately corrected for drift over time.

In a galvanic cell type gas sensor, the potential of the working electrode greatly depends on the potential of the counter electrode. That is, in the galvanic cell type gas sensor, the type of the gas to be detected is determined by the counter electrode selected. Therefore, the present invention is a galvanic cell type gas sensor in which a plurality of different counter electrodes are provided for one working electrode so that one of the counter electrodes can be selected corresponding to each gas to be detected. Accordingly, the present invention does not require an external electric source and is suitable for measurement of a plurality of gasses. In realizing the present invention, it is important to know the equilibrium potential (VH) of hydrogen in the electrolytic solution used, the equilibrium potential (VO) of oxygen in the electrolytic solution, the equilibrium potentials (V1, V2, ... Vn) of the N counter electrodes, and the diffusion-controlling rate regions (V1′−VH, V2′-VH, ... Vn′−VH or V1′−VO, V2′−VO, ... Vn′−VO) in the working electrode for the N gasses to be detected. The diffusion-controlling rate region of a particular gas is defined as a voltage region in which the velocity of a chemical reaction (for example, oxidation or reduction) is controlled by the diffusion velocity of a material. For the purpose of simplification, a sensor for detecting two kinds of gasses, that is, a sensor having two kinds of counter electrodes, will be described below. However, it will be apparent that the invention can be applied to the detection of a plurality of gasses by utilizing a corresponding number of counter electrodes.

Assuming that the oxidizing gasses to be measured are respectively represented by A and B and that the working electrode is energized while the respective gasses are placed in contact with the working electrode, then the potential of the working electrode changes as shown in FIG. 3 which illustrates the relationship between the current through a working electrode and the voltage of the working electrode with respect to a Standard Hydrogen Electrode (SHE). VH represents the equilibrium potential of hydrogen. When the potential is lower than VH, hydrogen is produced from the working electrode. With respect to the gas A, the region between Va′ and VH is the diffusion-controlling rate region of a gas A. With respect to the gas B, the region between Vb′ and VH is the diffusion-controlling rate region of a gas B. Within the gas diffusion-controlling rate regions the respective gas concentration is proportional to current through the electrode. Accordingly, the counter electrode must be selected so that, in the case of the gas A, the equilibrium potential thereof is higher than VH and lower than Va′ and, in the case of the gas B, the equilibrium potential thereof is higher than VH and lower than Vb′. Further, because the gasses A and B may be coexistent, the counter electrode for the gas A must have a higher potential than VB" to avoid the influence of the gas B.

Thus, counter electrodes, respectively having equilibrium potentials Va and Vb, are respectively selected for the gasses A and B. Accordingly, the working electrode and the first counter electrode are connected through a resistor for detection of the gas A and, on the other hand, the working electrode and the second counter electrode are connected through a resistor for detection of the gas B. In this case, the potential of the working electrode successively changes to $Va+iR$ and $Vb+iR$. Therefore, in selection of the resistor, it is necessary that the potential across the resistor is respectively small so as to maintain a voltage of the working electrode which is smaller than Va' and Vb'. If necessary, different resistors R may be provided for the counter electrodes.

DETAILED DESCRIPTION OF THE PREFERRED EMBODIMENTS

Figure 1:
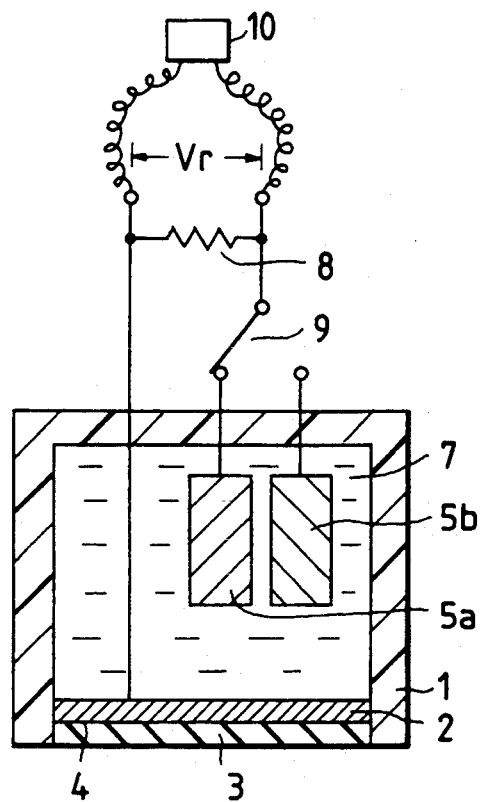
FIG. 1 is a sectional view of a galvanic cell type gas sensor according to a first embodiment of the present invention.

The present invention will be described below with respect to preferred embodiments thereof. FIG. 1 is a sectional view of a galvanic cell type gas sensor according to a first preferred embodiment of the present invention. The sensor has a container body 1 formed from ABS resin or the like, a working electrode 4, which consists of a catalyst electrode 2 formed by electrodepositing platinum on porous carbon, and a diaphragm 3 provided on the outside thereof and formed from tetrafluoroethylene-hexafluoropropylene copolymer. A counter electrode 5a is formed from lead and a counter electrode 5b is formed from lead dioxide. An electrolytic solution 7, consisting of a mixture of an aqueous solution of acetic acid, lead acetate and potassium acetate, is contained in the container body 1.

Figure 4:
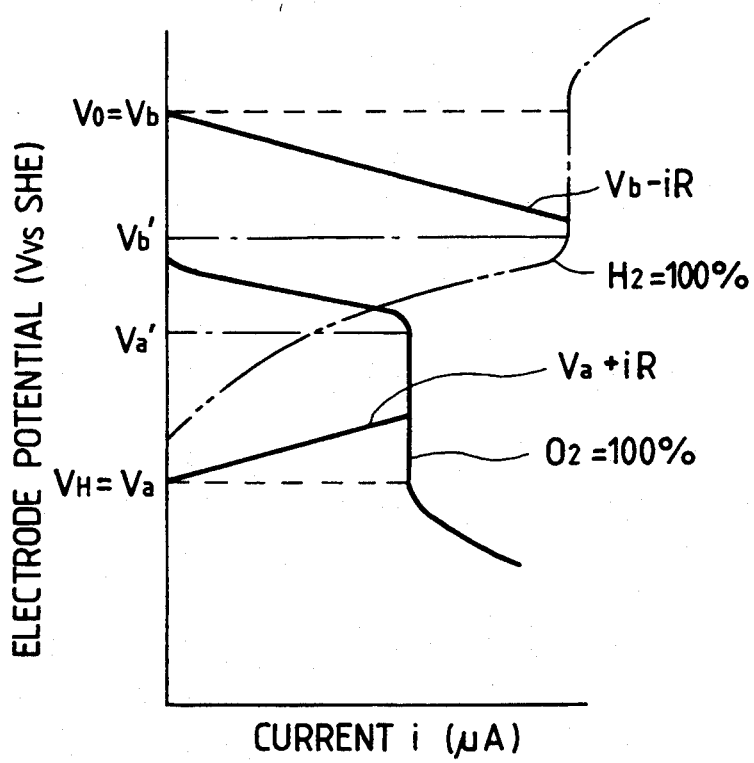
FIG. 4 is a graph showing the relationship between electrode potential and current in the first embodiment.

The working electrode 4 and one of the counter electrodes 5a and 5b are connected through a resistor 8. A desired one of the counter electrodes 5a and 5b is selected by a changeover switch 9. The relations between the respective equilibrium potentials Va and Vb, of the counter electrodes 5a and 5b, and the equilibrium potentials VO and VH of oxygen and hydrogen and the potential changes where the working electrode is energized while bringing oxygen or hydrogen into contact with the working electrode are illustrated in FIG. 4. FIG. 4 also illustrates the relationship between current through working electrode 4 and the voltage of working electrode 4 with respect to a Standard Hydrogen Electrode (SHE).

As shown in FIG. 4, the diffusion-controlling rate region of oxygen is between Va' and $VH=Va$ and the diffusion-controlling rate region for hydrogen is between Vb' and $VO=Vb$, respectively. The counter electrodes 5a and 5b for detecting oxygen and hydrogen, respectively, are selected so as to have equilibrium potentials that are within the aforementioned diffusion-controlling regions. The potential of the working electrode 4 changes to $Va+iR$ or $Vb-iR$ according to the current i flowing through the detection resistor 8. It is important to note that the counter electrodes are selected so that the potential does not deviate from each of the diffusion-controlling regions for the respective gasses. The diffusion determining rates as well as proper selection of electrode materials and resistance values can readily be determined by one skilled in the art.

Figure 2:
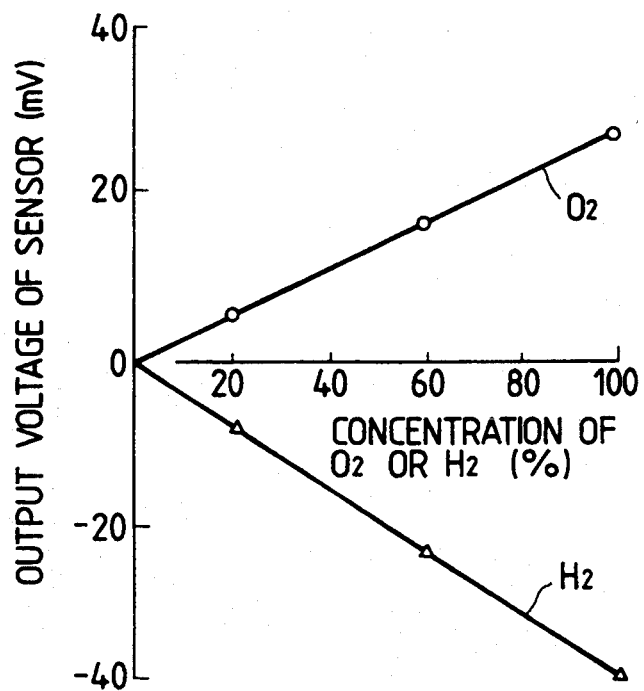
Fig. 2 is a graph showing the relationship between the concentration of oxygen in nitrogen or hydrogen in air and the output voltage from the sensor.

An output voltage Vr is detected between opposite ends of the detection resistor 8, by voltage detector 10 (see FIG. 1). FIG. 2 illustrates the output voltage Vr when the galvanic cell type sensor is placed in an atmosphere of nitrogen respectively containing 20%, 60% and 100% of oxygen ($O_2$) concentration, after selecting the electrode 5a of lead by the changeover switch 9, and the same output voltage when the galvanic cell type sensor is placed in an atmosphere of air respectively containing 20%, 60% and 100% of hydrogen ($H_2$) (as combustible gas) concentration, after selecting the electrode 5b of lead dioxide by the changeover switch 9, are plotted in FIG. 2. It is apparent from FIG. 2 that the galvanic cell type sensor according to the present invention can detect various gasses through a simple operation of selecting the desired counter electrodes and measurement of the voltage drop across resistor 8. In other words, as illustrated in FIG. 2, the voltage Vr across the resistor 8 is proportional to the concentration of gas which corresponds to the selected electrode. Accordingly, gas concentration can be easily determined by a simple algorithm executed by a micro-computer or the like.

Figure 5:
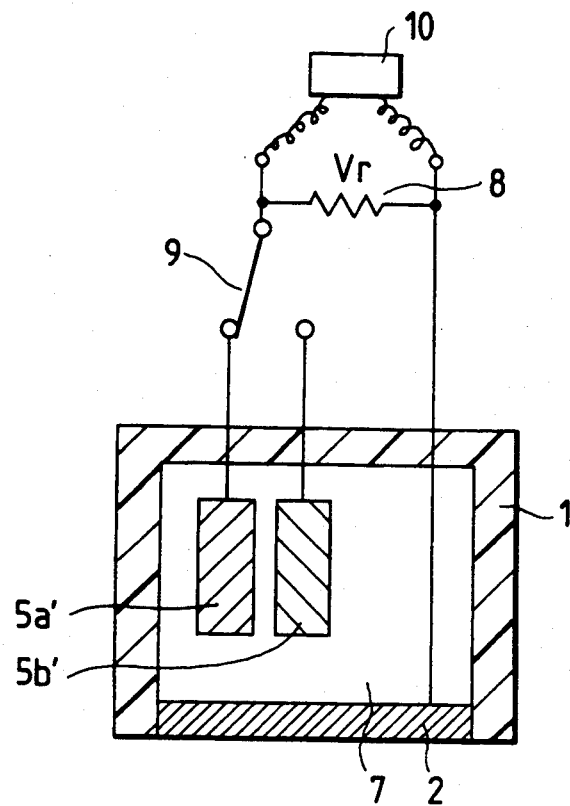
FIG. 5 is a sectional view of a galvanic cell type gas sensor according to a second embodiment of the invention.
Figure 6:
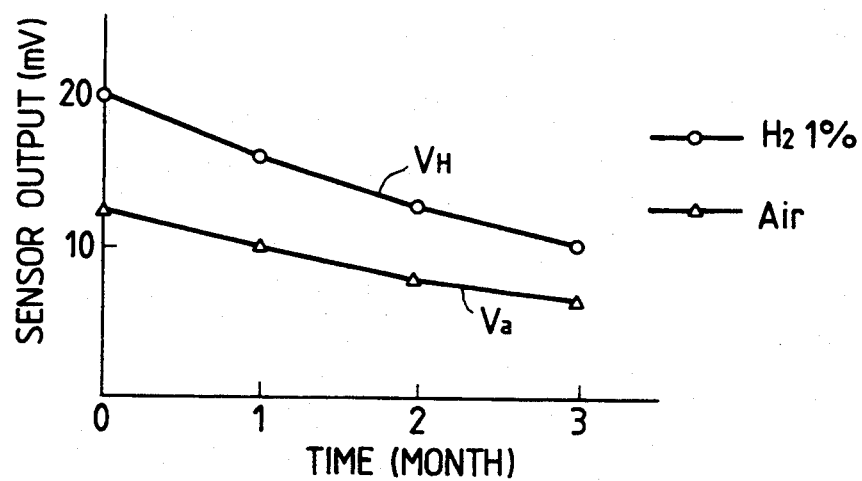
FIG. 6. is a graph illustrating the change in output voltages of the second embodiment with respect to time.
Figure 7:
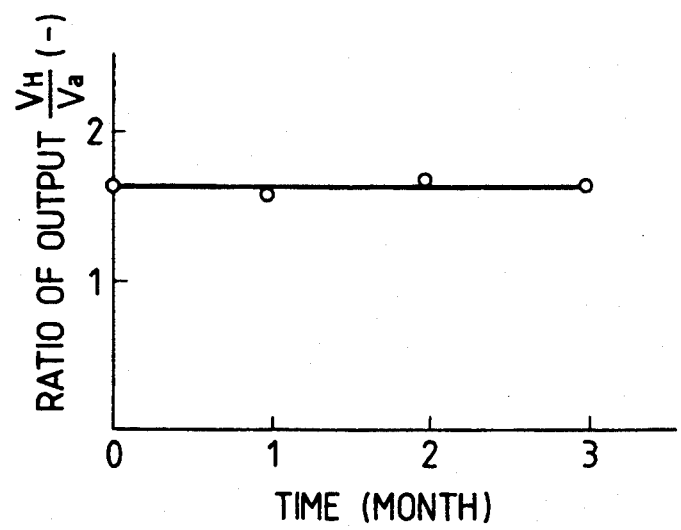
FIG. 7 is a graph illustrating the relationship between the curves of FIG. 6.

A second embodiment of the invention is illustrated in FIG. 5. This embodiment provides correction to a measured gas concentration value so as to compensate for drift over time. Main causes of the drift of the galvanic cell type concentration meter with the passage of time are deterioration of the diaphragm and loosening of contact between the diaphragm and the catalyst electrode. Because these causes act evenly regardless of the type of gas, the drift of the measured value of oxygen concentration can be applied to correct the drift of the measured value of concentration of another gas if the drift of oxygen concentration can be measured. Assuming that an output voltage Vr measured across resistor 8 by voltage detector 10 ,in the case of connection of one counter electrode for oxygen in air and the working electrode, through resistor 8, is represented by Va and that an output voltage in the case of connection of the other counter electrode and the working electrode, while the gas x to be detected is present, is represented by Vx, then gas concentration Cx is represented by the following formula:

$$Cx = R \times Vx \div Va \quad (1)$$

in which R is a constant as obtained initially on the basis of output voltages Vr using known oxygen and gas concentrations.

The specific structure and operation of the second preferred embodiment of the invention will be described below. In FIG. 5, a container 1 is formed from ABS resin, or the like. A working electrode 2 composed of a catalyst electrode formed by electrodepositing platinum on porous carbon and a diaphragm provided on the outside thereof and formed from tetrafluoroethylene-hexafluoropropylene copolymer, is disposed across an opening of the container. A hydrogen counter electrode $5a'$, formed from lead dioxide, and an oxygen counter electrode $5b'$ formed from lead are disposed in the container 1 and surrounded by electrolytic solution 7 formed of a mixture aqueous solution of acetic acid, potassium acetate and lead acetate. The working electrode 2 and one of the counter electrodes $5a'$ and $5b'$ are electrically connected through the resistor 8. The counter electrodes $5a'$ and $5b'$ are selected by a changeover switch 9 so that, for measurement of hydrogen gas, the working electrode 2 is connected to the counter electrode $5a'$ and for correction of the concentration meter, the working electrode 2 is connected to the counter electrode $5b'$.

Figure 3:
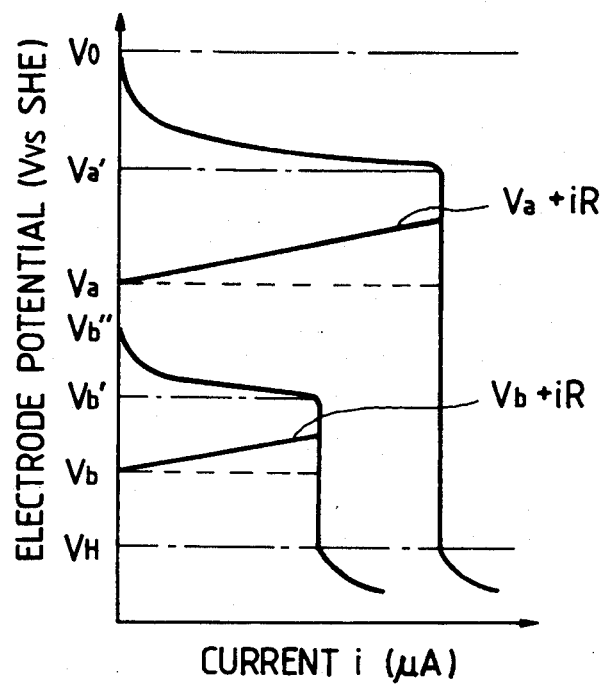
Fig. 3 is a graph showing the relationship between electrode potential and current.

The change of the output voltage Vr=VH (in the case of use of the counter electrode $5a'$) at hydrogen concentration 1% and the change of the output voltage Vr=Va (in the case of use of the counter electrode $5b'$) in air, with respect to time, are illustrated in FIG. 2. The change of the ratio of VH to Va is illustrated in FIG. 3. As is apparent from FIG. 2, the outputs from the concentration meter are respectively reduced with the passage of time t. However, as shown in FIG. 3, the ratio VH/Va remains essentially constant. That is, the drift of hydrogen concentration is proportional to the drift of oxygen concentration and thus it is possible to correct the drift of hydrogen concentration by measuring the oxygen concentration in air and utilizing the above-mentioned equation (1), or any other appropriate equation. Of course the equations can be determined experimentally or empirically executed by a micro-computer or the like.

As described above, the second embodiment provides a galvanic cell type gas concentration meter in which correction in air can be performed. Accordingly, the gas concentration meter can be operated without the need for a standard gas.

In particular, by selectively utilizing a plurality of counter electrodes, each having, an equilibrium potential which is within the diffusion-controlling region of a particular gas to be detected, a plurality of gasses can be detected by a single sensor merely by detecting the voltage drop across a resistor. Also, a detection value of a gas can easily be corrected for drift over time.

Figure 8:
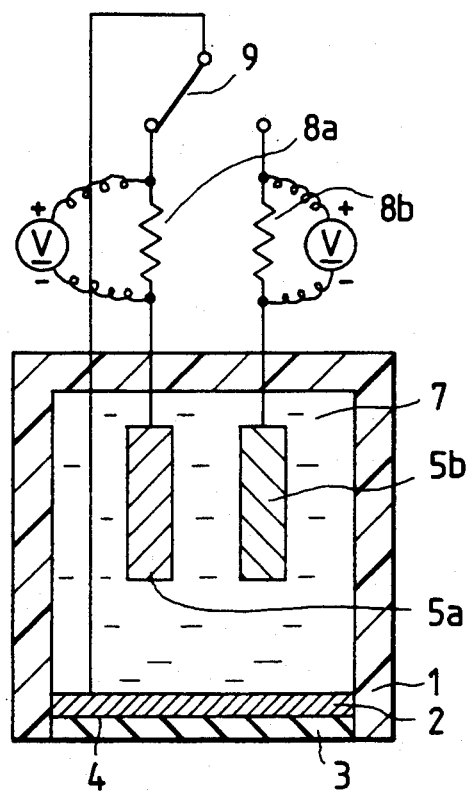
FIG. 8 is a sectional view of a galvanic cell type gas sensor of a third embodiment of the present invention.
Figure 10:
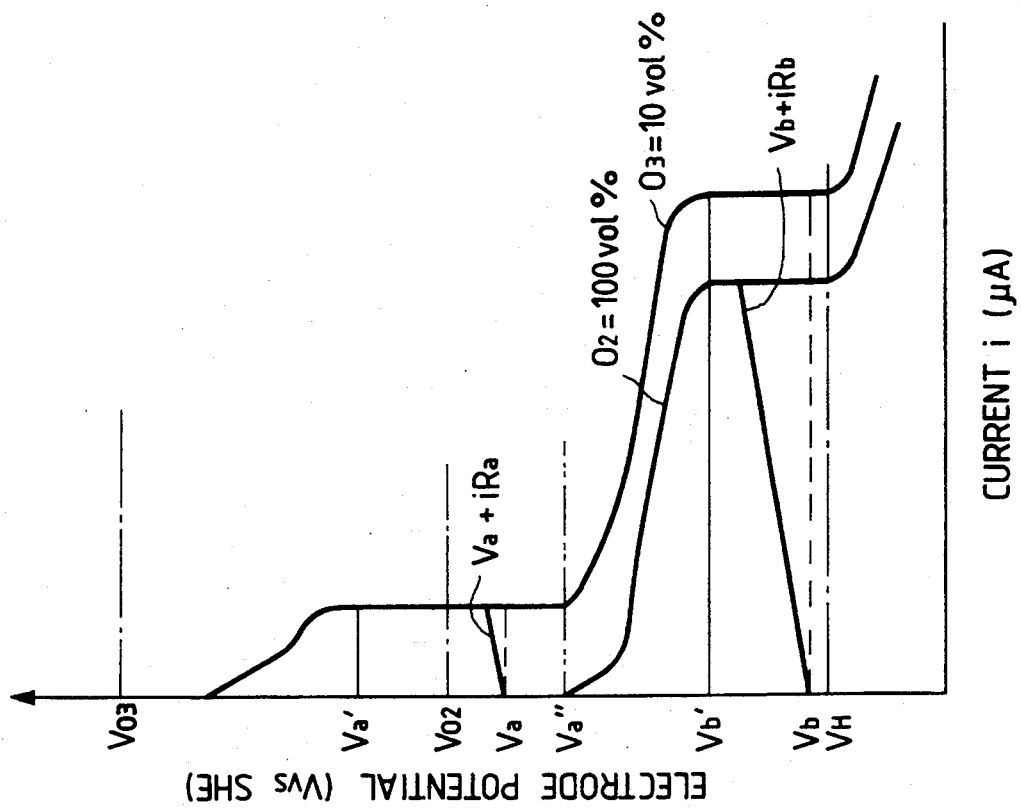
FIG. 10 a graph showing the relationship between electrode potential and current.

A third preferred embodiment of the present invention will be described. FIG. 8 is a sectional view of a galvanic cell type gas sensor according to the third embodiment of the present invention. The sensor comprises a container body 1 formed of vinyl chloride resin, a working electrode 4, which consists of a catalyst electrode 2 formed by evaporating gold on porous carbon and a diaphragm 3 provided on the outside thereof and made of tetrafluoroethylene-hexafluoropropylene copolymer, a counter electrode $5a$ of silver-silver chloride, a counter electrode $5b$ of lead, and an electrolytic solution 7 consisting of a mixture of an aqueous solution of potassium chloride and potassium hydroxide. The working electrode 4 and the counter electrode $5a$ or $5b$ are connected through a detection resistor $8a$ or $8b$. A desired one of the counter electrodes $5a$ and $5b$ is selected by a changeover switch 9. FIG. 10 shows the relations between the respective equilibrium potentials Va and Vb of the counter electrodes $5a$ and $5b$, and equilibrium potentials $V_{O3}$ and $V_{O2}$ of ozone 10 vol % (remainder: oxygen) and oxygen, and the potential changes where the working electrode is energized while bringing the ozone or oxygen into contact with the working electrode.

As shown in FIG. 10, the diffusion-controlling region of ozone and oxygen are Va'−Va and Vb'−Vb, respectively. The equilibrium potentials of the counter electrode $5a$ for detecting ozone and the counter electrode $5b$ for detecting oxygen are within the diffusion-controlling regions.

Two diffusion-controlling regions are seen in the potential change of ozone 10 vol% (remainder: oxygen) because reduction reaction of only ozone occurs at a potential higher than Va'', and reduction reaction of ozone and oxygen occurs at a potential lower than Va'' and higher than Vb.

Figure 9:
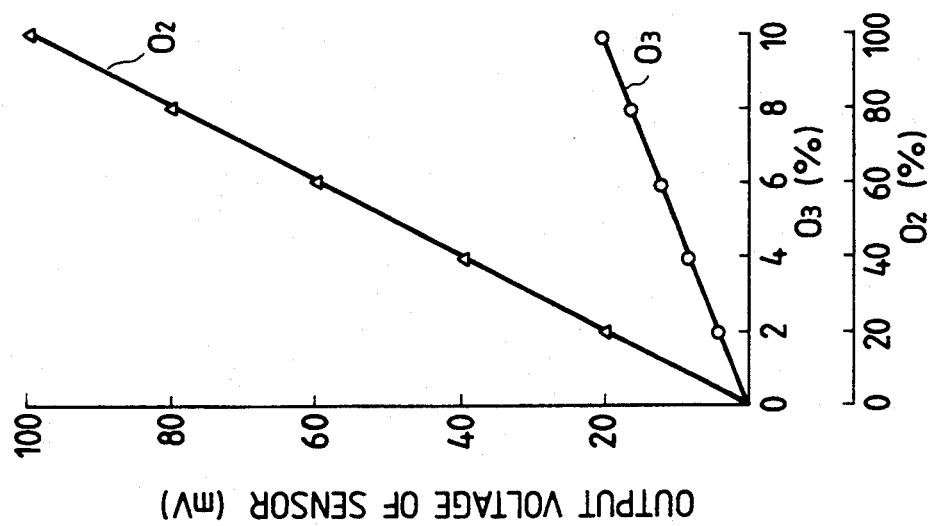
FIG. 9 is a graph showing the relationship between the concentration of ozone in oxygen or oxygen in nitrogen and the output voltage from the sensor.

The potential of the working electrode changes to Va+iRa or Vb+iRb according to the current i flowing through the detection resistor $8a$ or $8b$, which does not deviate from each of the diffusion-controlling regions for the respective gases. FIG. 9 shows the output voltage detected between opposite ends of the detection resistor $8a$ when the galvanic cell type sensor is placed in an atmosphere of oxygen respectively containing 2, 4, 6, 8 and 10% of ozone concentration after selecting the counter electrode $5a$ of silver-silver chloride by the changeover switch 9, and the output voltage detected between the opposite ends of the detection resistor $8b$ when the galvanic cell type sensor is placed in an atmosphere of nitrogen respectively containing 20, 40, 60, 80 and 100% of oxygen ($O_2$) concentration after selecting the counter electrode $5b$ of lead by the changeover switch 9. From FIG. 10, it is understood that the galvanic cell type sensor of the present invention can detect various gases by simply switching the counter electrodes.

The invention has been described through preferred embodiments. However, it will be apparent to those skilled in the art that various modifications can be made without departing from the scope of the invention as defined by the appended claims.

We claim:

1. A diaphragm galvanic cell gas sensor, comprising:
   a single container having an electrolytic solution therein;
   only a single working electrode disposed in said single container, said working electrode being made of a material which provokes one of an oxidation and reduction reaction in a number of different objective gases to be detected, said working electrode being free of any externally applied voltage;
   a plurality of counter electrodes equal in number to said number of objective gases and disposed in said single container, each of said counter electrodes corresponding to only a particular one of said objective gases to be detected, said counter electrodes each being made of a material which has an equilibrium potential which is within a diffusion-controlling rate region of only a respective one of said objective gases;

a diaphragm covering an open end of said container and limiting supply of the gases thereto; and means for selecting a counter electrode by placing an electrical conduction path between said working electrode and the selected counter electrode to produce an electrical signal indicative of the objective gas corresponding to the selected counter electrode, a first of said counter electrodes being made of lead dioxide and a second of said counter electrodes being made of lead.

2. A diaphragm galvanic cell gas sensor, comprising:

a single container having an electrolytic solution therein;

only a single working electrode disposed in said single container, said working electrode being made of a material which provokes one of an oxidation and reduction reaction in a number of different objective gases to be detected, said working electrode being free of any externally applied voltage;

a plurality of counter electrodes equal in number to said number of objective gases and disposed in said single container, each of said counter electrodes corresponding to only a particular one of said objective gases to be detected, said counter electrodes each being made of a material which has an equilibrium potential which is within a diffusion-controlling rate region of only a respective one of said objective gases;

a diaphragm covering an open end of said container and limiting supply of the gases thereto; and means for selecting a counter electrode by placing an electrical conduction path between said working electrode and the selected counter electrode to produce an electrical signal indicative of the objective gas corresponding to the selected counter electrode;

a first of said counter electrodes being made of silver-silver chloride and a second of said counter electrodes being made of lead.

3. A diaphragm galvanic cell gas sensor, comprising:

a single container having an electrolytic solution therein;

only a single working electrode disposed in said single container, said working electrode being made of a material which provokes one of an oxidation and reduction reaction in a number of different objective gases to be detected, said working electrode being free of any externally applied voltage;

a plurality of counter electrodes equal in number to said number of objective gases and disposed in said single container, each of said counter electrodes corresponding to only a particular one of said objective gases to be detected, said counter electrodes each being made of a material which has an equilibrium potential which is within a diffusion-controlling rate region of only a respective one of said objective gases;

a diaphragm covering an open end of said container and limiting supply of the gases thereto;

means for selecting a counter electrode by placing an electrical conduction path between said working electrode and the selected counter electrode to produce an electrical signal indicative of the objective gas corresponding to the selected counter electrode, a resistor disposed in said electrical conduction path;

means for measuring a voltage across said resistor and generating at least one measurement signal which is representative of a concentration of one of said objective gases; and means for determining a concentration of each of said objective gases based upon said measurement signal;

said measuring means adapted to generate a first measurement signal when a first of said counter electrodes, which corresponds to the detection of a first of said objective gases except oxygen, is selected, said measuring means adapted to generate a second measurement signal when a second of said counter electrodes, which corresponds to the detection of oxygen in air, is selected, said determining means adapted to utilize said second measurement signal to correct said first measurement signal for drift over time.

4. A sensor as claimed in claim 3, said first of said objective gases is hydrogen.

5. A sensor as claimed in claim 3, said first of said objective gases is ozone.

* * * * *